United States Patent [19]

Wetz

[11] Patent Number: 4,821,743
[45] Date of Patent: Apr. 18, 1989

[54] REMOVABLE IN-SHOE ANKLE BRACE

[76] Inventor: Hans-Henning Wetz, Im Schwiendahl 46, D-5880 Lüdenscheid, Fed. Rep. of Germany

[21] Appl. No.: 87,059

[22] Filed: Aug. 19, 1987

[51] Int. Cl.⁴ ............................................... A61F 5/30
[52] U.S. Cl. ........................................ 128/893; 36/89
[58] Field of Search ............... 128/80 D, 80 E, 80 H, 128/80 J, 149, 153, 165, 166, 166.5

[56] References Cited

U.S. PATENT DOCUMENTS

| | | | |
|---|---|---|---|
| D. 255,384 | 6/1980 | Finnieston | 128/90 |
| D. 272,281 | 1/1984 | Alush | 128/89 R |
| 938,440 | 10/1909 | Sescila | 128/166 |
| 1,564,874 | 12/1925 | Madden | 128/165 |
| 1,858,162 | 5/1932 | MacNamee | 128/165 |
| 3,856,008 | 12/1974 | Fowler et al. | 128/165 |
| 4,197,845 | 4/1980 | Browning | 128/153 |
| 4,401,113 | 8/1983 | Incorvaia | 128/165 |
| 4,494,536 | 1/1985 | Latenser | 128/153 |

Primary Examiner—Robert A. Hafer
Assistant Examiner—Charles H. Sam
Attorney, Agent, or Firm—Herbert Dubno; Andrew Wilford

[57] ABSTRACT

An ankle-joint brace is formed as a tube of a heat-shapable synthetic resin formed along its full length on one side with a throughgoing entry slot. The tube is sufficiently deformable that the slot can be spread widely enough to accommodate a patient's ankle region. This slot allows the flexible brace to be opened up enough to be removed. The tube is further formed with a heel seat complementary to the patient's heel and a sole part extending forwardly from the heel seat and complementary to the distal surface of the patient's instep. In addition it is formed with an instep part complementary to the proximal surface of the patient's instep, bounding part of the slot, and joined on the side opposite the slot to the sole part. Opposite the slot the tube is formed with a window accommodating the respective prominence of the patient's calcaneous and the slot is widened similarly to accommodate the respective prominence of the patient's calcaneous.

6 Claims, 1 Drawing Sheet

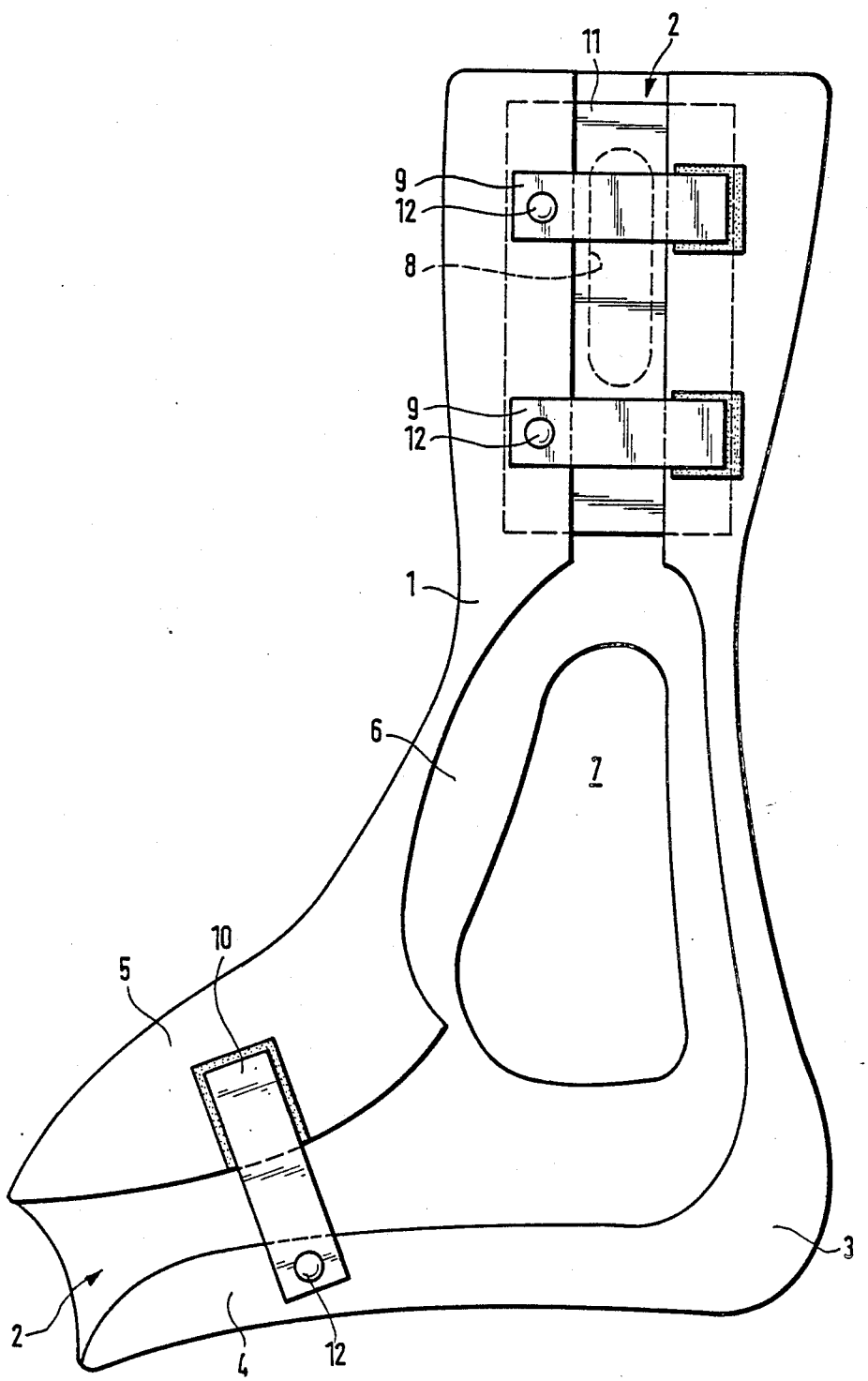

2

REMOVABLE IN-SHOE ANKLE BRACE

FIELD OF THE INVENTION

The present invention relates to an ankle brace or splint. More particularly this invention concerns such a brace which is removable and which can be worn within a shoe.

BACKGROUND OF THE INVENTION

The ankle joints between the foot and lower leg are subject to arthritic and other kinds of degeneration and to trauma, whether accidental or surgically done as in an ankle fusion. The treatments of these problems invariably require that the upper and lower joints be held still while they heal. Good medical practice avoids unnecessary immobilization of a patient, so that it is necessary to protect the joints while permitting the patient to resume as much as possible of his or her daily routine.

Thus an ankle brace must, while holding the bones proximal and distal of the joints relatively immobile, be wearable under normal clothing. Furthermore hygiene requires that the brace be removable. Nothing now known has the strength necessary for health reasons and the small size necessary for cosmetic reasons, while still being removable for hygiene reasons.

OBJECTS OF THE INVENTION

It is therefore an object of the present invention to provide an improved ankle brace.

Another object is the provision of such an ankle brace which while being strong and compact is also removable.

SUMMARY OF THE INVENTION

An ankle-joint brace according to the invention is formed as a tube of a heat-shapable synthetic resin formed along its full length on one side with a throughgoing entry slot. The tube is sufficiently deformable that the slot can be spread widely enough to accommodate a patient's ankle region. This slot allows the flexible brace to be removed, yet does not substantially weaken it.

According to another feature of this invention the tube is further formed with a heel seat complementary to the patient's heel and a sole part extending forward from the heel seat and complementary to the distal surface of the patient's instep. In addition it is formed with an instep part complementary to the proximal surface of the patient's instep, bounding part of the slot, and joined on the side opposite the slot to the sole part. Opposite the slot the tube is formed with a window accommodating the respective prominence of the patient's calcaneous and the slot is widened similarly to accommodate the oposite prominence of the calcaneous.

Thus the brace of this invention is complementary internally to the patients foot, but is cut away at the critical joint regions, since such a brace is typically used on an ankle that is swollen or particularly sensitive.

To facilitate donning the brace according to this invention the tube is formed opposite the slot and proximal of the window with a longitudinally extending and throughgoing elongated second window of oval shape. The brace is normally held closed by openable and closable fasteners extending across the slot both distally and proximally of the widened region of the slot.

To avoid pinching the soft-tissue of the leg, the brace has a flexible and thin sheet secured to one side of the slot inside the tube and sufficiently large to reach past the other side of the slot when the brace is in place on the patient's ankle region.

DESCRIPTION OF THE DRAWING

The above and other objects, features, and advantages will become more apparent from the following, reference being made to the accompanying drawing whose sole figure is a lateral view of the brace according to this invention.

SPECIFIC DESCRIPTION

As seen in the drawing a brace according to this invention is basically unitarily formed of a heat-shapable resin so as to be internally complimentary to the patient's ankle joint. It is formed basically as a tube 1 sufficiently long distally to reach past the distal bones of the ankle joints and proximally up the tibia and fibula somewhat and open along its full length on the media side at a slot 2. The tube 1 forms a seat 3 for the heel and a sole 4 for the underside of the instep. On the other side of the slot 2 the tube 1 forms an instep-covering shell 5 joined to the sole part 4 on the lateral side of the brace.

Medially the slot 2 is enlarged at 6 to accommodate the medial prominence of the calcaneous and any other ankle-joint bones, and oppositely distally the tube 1 is formed with a somewhat smaller window 7 accommodating mainly the lateral prominence. Both windows or enlargements 6 and 7 are also dimensioned to give clearance for swollen or sensitive soft tissue.

The leg or proximal part of the tube 1 is formed on the lateral surface opposite and in line with the slot 2 with an elongated throughgoing aperture 8. The function of this aperture 8 is both to improve the bendability of the tube 1 along a line on its lateral surface directly opposite the slot 2 and bisecting the windows 7 and 8 and to accommodate possibly swollen soft tissue. The heat-shapable resin of the tube 1 is sufficiently pliant at room temperature to allow the boot of this invention to be opened up at the medial slot 2 sufficiently to slip the foot and ankle into it without hurting the ankle. The elasticity of the resin forming the tube 1 is sufficient to allow it to close up snugly once the foot is inside it.

From the top of the brace as seen in the drawing to the bottom of the heel seat 3 the brace according to this invention is about 25 cm tall in a 40 or 41 (West German system) shoe size.

Once the tube 1 has been opened and fit around the joint to be braced, the slot 2 is kept closed by Velcro-type hook-and-barb fasteners 9 and 10 each having a tape riveted at 12 to one side of the slot 2 and a patch adhered to the other. The two fasteners 9 are provided spaced longitudinally apart on the proximal leg-part of the brace above the enlargement 6 and the identical fastener 10 is provided between the instep shell 5 and sole 4.

In order to avoid pinching soft tissue of the leg in the proximal upper part of the slot 2 a flexible and thin sheet 11 is secured by the rivets 12 of the upper fasteners 9 inside the tube 1 to the ventral side of the slot 2. Once the brace is fitted to the foot, this sheet 11 is tucked inside the tube 1 on the dorsal side of the slot 2. Then the brace is snugged on the leg and foot and all the fasteners 9 and 10 are closed, the fasteners 9 closing backward and the fastener 10 upward. The sheet 11 allows the slot 2 to be closed without pinching soft tissue of the lower leg.

Such a brace can be made so very thin that it can be worn within a shoe and even under a sock. It protects the patient's ankle while permitting him to dress normally and as much as possible resume a normal life in spite of an ankle that would be unable to support him or her unassisted.

I claim:

1. An ankle-joint brace formed as a tube of a heat-shapable synthetic resin formed internally complementarily to a shape corresponding to the external surface of the lower region of a human leg terminating in a foot and formed along its full length on one side of the foot portion of the shape with a throughgoing entry slot, the tube being sufficiently deformable that the slot can be spread widely enough to accommodate a patient's ankle region, the tube being formed with an upwardly and inwardly concave heel seat complementary to the heel portion of the shape and a sole part extending forward from the heel seat and forming a flat support surface complementary to the distal surface of the foot portion of the shape, and a downwardly and inwardly concave instep part complementary to the proximal surface of the foot portion of the shape, bounding part of the slot, and joined on the side of the foot portion of the shape opposite the slot to the sole part, the tube being substantially closed over the top of the foot portion of the shape and at the front of the ankle portion of the shape.

2. The ankle-joint brace defined in claim 1 wherein the tube is formed opposite the slot with a window accommodating the respective prominence of the patient's calcaneous and the slot is widened similarly to accommodate the respective prominence of the patient's calcaneous.

3. The ankle-joint brace defined in claim 2 wherein the tube is formed opposite the slot and proximal of the window with a longitudinally extending and throughgoing elongated second window.

4. The ankle-joint brace defined in claim 3, further comprising openable and closable fasteners extending across the slot both distally and proximally of the widened region of the slot.

5. The ankle-joint brace defined in claim 3, further comprising a flexible and thin sheet secured to one side of the slot inside the tube and sufficiently large to reach past the other side of the slot when the brace is in place on the patient's ankle region.

6. An ankle-joint brace comprising:

a tube unitarily formed internally complementarily to a shape corresponding to the external surface of a human leg terminating in a foot and formed of a heat-shapable synthetic resin with a slot extending along full length on the medial side of the shape with a throughgoing entry slot, an upwardly and inwardly concave heel seat complementary to the portion of the shape, an upwardly directed sole part extending forward from the heel seat and complementary to the distal surface of the instep portion of the shape, an inwardly and downwardly concave instep part complementary to the proximal surface of the instep portion of the shape, bounding part of the slot, and joined on the lateral side of the leg portion of the shape to the sole part, a window on the lateral side of the leg portion of the shape and accommodating the lateral prominence of the calcaneous portion of the shape, the slot being widened similarly to accommodate the medial prominence of the calcaneous portion of the shape, and a longitudinally extending and throughgoing elongated second window on the lateral side of the leg portion of the shape distal of the first-mentioned window, the tube being sufficiently deformable that the slot can be spread widely enough to accommodate a patient's ankle region, the tube being substantially closed over the top of the foot portion of the shape and at the front of the ankle portion of the shape, openable and closable fasteners extending across the slot both distally and proximally of the widened region of the slot; and a flexible and thin sheet secured to one side of the slot inside the tube and sufficiently large to reach past the other side of the slot when the brace is in place on the patient's ankle region.

* * * * *